United States Patent
Ahmad et al.

(10) Patent No.: US 7,005,408 B2
(45) Date of Patent: Feb. 28, 2006

(54) WARMING AND NONIRRITATING LUBRICANT COMPOSITIONS AND METHOD OF COMPARING IRRITATION

(75) Inventors: Nawaz Ahmad, Monmouth Junction, NJ (US); Ying Sun, Belle Mead, NJ (US); Shun Y. Lin, Plainsboro, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 10/137,509

(22) Filed: May 1, 2002

(65) Prior Publication Data

US 2003/0207772 A1 Nov. 6, 2003

(51) Int. Cl.
*C10M 105/14* (2006.01)
*A61K 9/06* (2006.01)

(52) U.S. Cl. ............... 508/219; 508/505; 508/583; 424/DIG. 14; 514/967

(58) Field of Classification Search .............. 508/583, 508/216
See application file for complete search history.

(56) References Cited

U.S. PATENT DOCUMENTS

| | | | |
|---|---|---|---|
| 4,110,426 A | | 8/1978 | Bamhurst et al. |
| 4,233,876 A | * | 11/1980 | Leahy et al. ............ 508/583 |
| 4,347,237 A | * | 8/1982 | Evenstad et al. ......... 424/78 |
| 4,636,520 A | | 1/1987 | Umio et al. |
| 4,720,507 A | | 1/1988 | Wiebe |
| 4,863,725 A | | 9/1989 | Deckner et al. |
| 4,950,475 A | | 8/1990 | Vishnupad et al. |
| 4,981,686 A | * | 1/1991 | Hardy ..................... 424/93 |
| 5,002,938 A | | 3/1991 | Wang et al. |
| 5,208,031 A | | 5/1993 | Kelly |

(Continued)

FOREIGN PATENT DOCUMENTS

| | | |
|---|---|---|
| EP | 0 027 730 A2 | 4/1981 |
| EP | 0 404 376 A2 | 12/1990 |
| EP | 0 581 581 A2 | 2/1994 |
| EP | 0 966 956 B1 | 12/1999 |
| ES | 2 074 030 B1 | 8/1995 |
| JP | 2-311408 A | 12/1990 |
| JP | 2001-335429 | 5/2000 |
| JP | 2001-335429 A | 12/2001 |
| WO | WO 98/18446 A | 5/1998 |
| WO | WO 98/18849 A | 6/1998 |
| WO | WO 99/28301 | 6/1999 |
| WO | WO 01/05400 A1 | 1/2001 |
| WO | WO 01/64176 A1 | 9/2001 |
| WO | WO 02/087570 A1 | 11/2002 |

OTHER PUBLICATIONS

Akin et al., "Continuous Low–Level Topical Heat in the Treatment of Dysmanorrhea.", Obstettrics & Gynecology, vol. 97, No. 3, pp 343–349 (Mar. 2001).

(Continued)

*Primary Examiner*—Ellen M. McAvoy

(57) ABSTRACT

This invention relates to substantially anhydrous warming, non-toxic and nonirritating lubricating compositions containing polyhydric alcohols and an insulating agent. The invention also relates to methods of using such compositions for lubrication, administration of active ingredients and for preventing or treating dysmenorrhea.

31 Claims, 5 Drawing Sheets

Epiderm Bioassay Results for Composition of the Invention (Example 1)

U.S. PATENT DOCUMENTS

| | | | |
|---|---|---|---|
| 5,236,609 A | | 8/1993 | Smith et al. |
| 5,270,032 A | | 12/1993 | Pollock et al. |
| 5,349,149 A | * | 9/1994 | Shiraki et al. .............. 508/583 |
| 5,393,528 A | | 2/1995 | Staab |
| 5,512,289 A | * | 4/1996 | Tseng et al. ................ 424/426 |
| 5,513,629 A | | 5/1996 | Johnson |
| 5,529,782 A | | 6/1996 | Staab |
| 5,595,980 A | | 1/1997 | Brode et al. |
| 5,599,551 A | | 2/1997 | Kelly |
| 5,658,583 A | | 8/1997 | Zhang et al. |
| 5,696,164 A | | 12/1997 | Sun et al. |
| 5,709,849 A | | 1/1998 | Ito et al. |
| 5,840,744 A | | 11/1998 | Borgman |
| 5,885,591 A | * | 3/1999 | Ahmad et al. .............. 424/400 |
| 5,895,658 A | | 4/1999 | Fossel |
| 5,902,593 A | * | 5/1999 | Kent et al. .................. 424/401 |
| 5,976,561 A | | 11/1999 | Kent et al. |
| 5,980,875 A | | 11/1999 | Mousa |
| 5,980,924 A | | 11/1999 | Yamazaki et al. |
| 6,007,846 A | | 12/1999 | Klar |
| 6,013,270 A | * | 1/2000 | Hargraves et al. .......... 424/401 |
| 6,019,782 A | | 2/2000 | Davis et al. |
| 6,060,077 A | | 5/2000 | Meignant |
| 6,139,848 A | * | 10/2000 | Ahmad et al. .............. 424/400 |
| 6,171,604 B1 | | 1/2001 | Mousa |
| 6,221,814 B1 | * | 4/2001 | Kaburagi et al. ........... 508/136 |
| 6,303,108 B1 | | 10/2001 | Boulier et al. |
| 6,641,825 B1 | | 11/2003 | Scholz et al. |
| 2002/0013304 A1 | | 1/2002 | Wilson et al. |
| 2002/0103414 A1 | | 8/2002 | Harrison et al. |
| 2003/0092754 A1 | | 5/2003 | Nishimuta et al. |

OTHER PUBLICATIONS

Fail et al., "General, Preproductive, Development, and Endocrine Toxicity of Boronated Compounds", Reproductive Toxicology, vol. 12, No. 1, pp 1–18 (1998).

Sun, "Skin Absorption Enhancement by Physical Means: Heat, Ultrasound, and Electricity", Chapter 10 of Transdermal and Topical Drug Delivery System, edited by Ghosh et al, Interpharm Press, Inc., pp 327–355 (1997).

Package—BIORE Cleanse Self–Heating Mask (front, back and side).

Package—Oil of Love AMASUTRA (front and back).

Remington: The Science and Practice of Pharmacy, Mach Publishing Company, 19$^{th}$ edition: 1995.

Water and Alcohol Mixtures and "The Amazing Air Bubble", Covenant Christian High School. 1999 http://htdconnect.com/–chargers/chem/seccwatalcohol.htm.

EP Communication dated Jul. 25, 2005 for EP application 03731070.3.

Digital photographs of package and package insert —Kamasutra Oil of Love.

PCT International Search Report dated Oct. 10, 2003, for corresponding PCT/US03/13475.

Kutteh W. et al.: "Vaghal lubricants for the Infertile couple: effect on sperm activity" International Journal of Fertility, Allan Press, Inc. Kansas, US vol. 41, No. 4, 1990, pages 400–404 XP000870083.

PCT Search Report dated Aug. 21, 2003, for PCT Appl. No. PCT/US 03/13554.

PCT Search Report dated Aug. 21, 2003, for PCT Appl. No. PCT/US 03/13478.

* cited by examiner

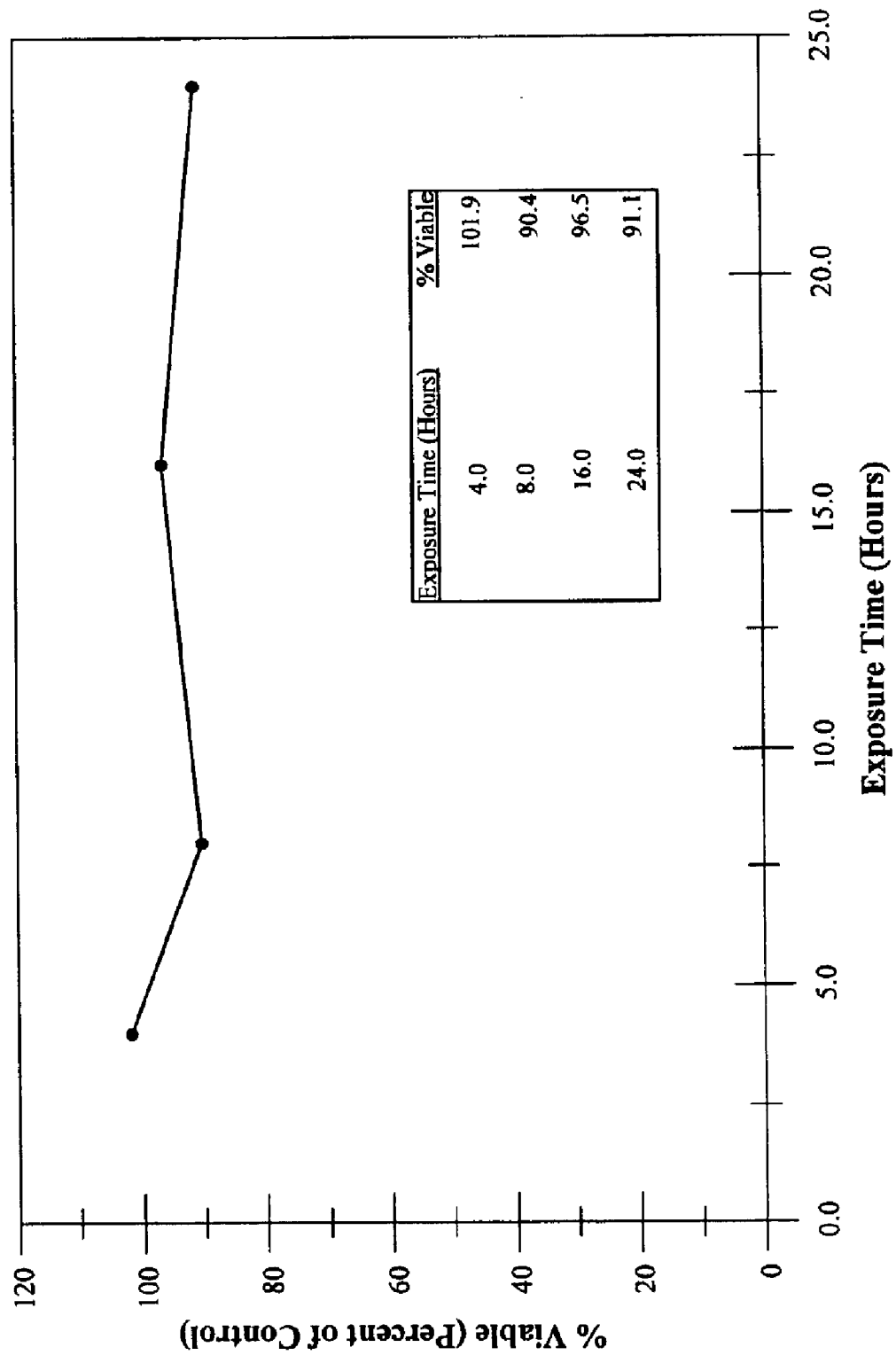

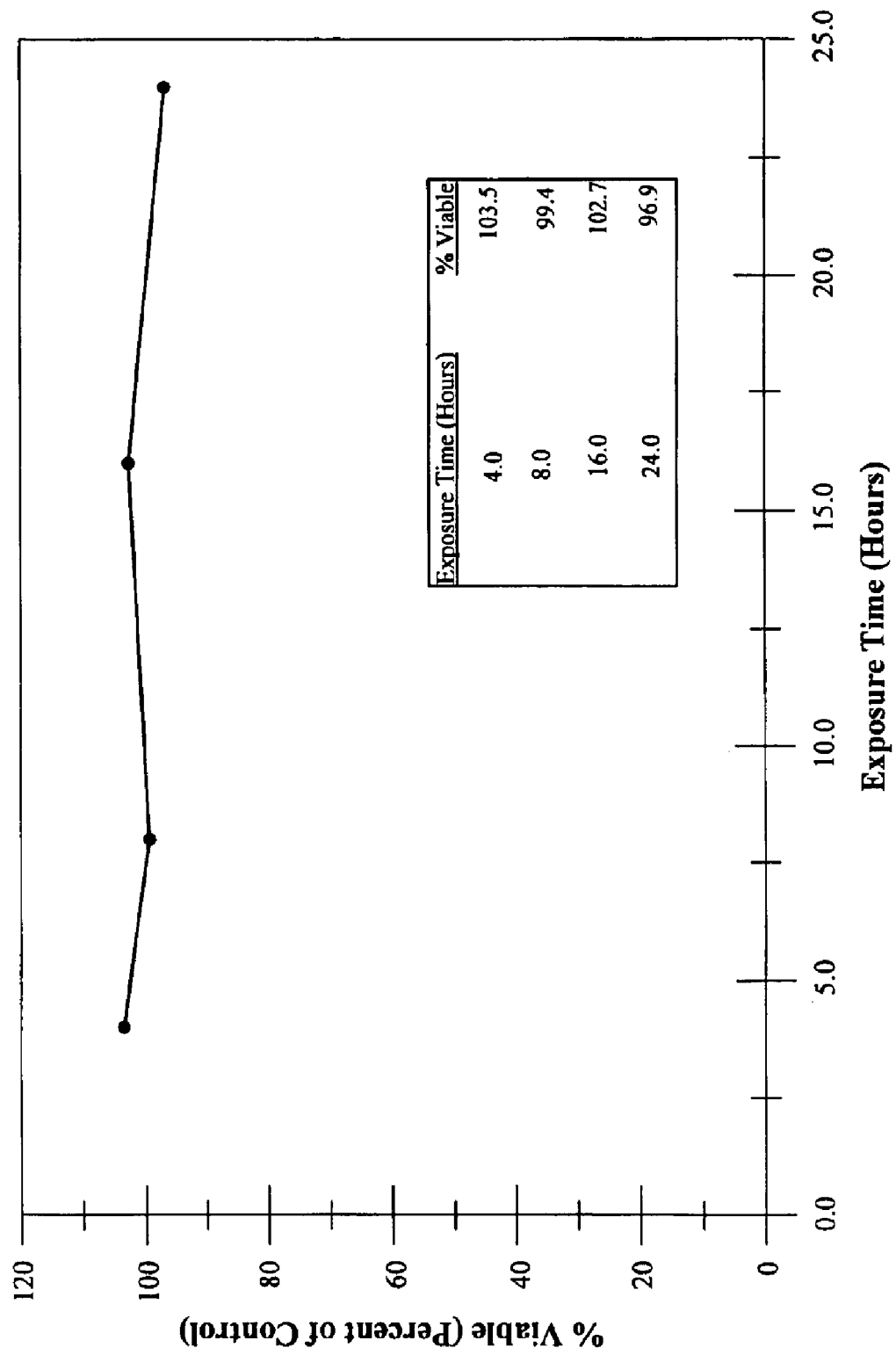

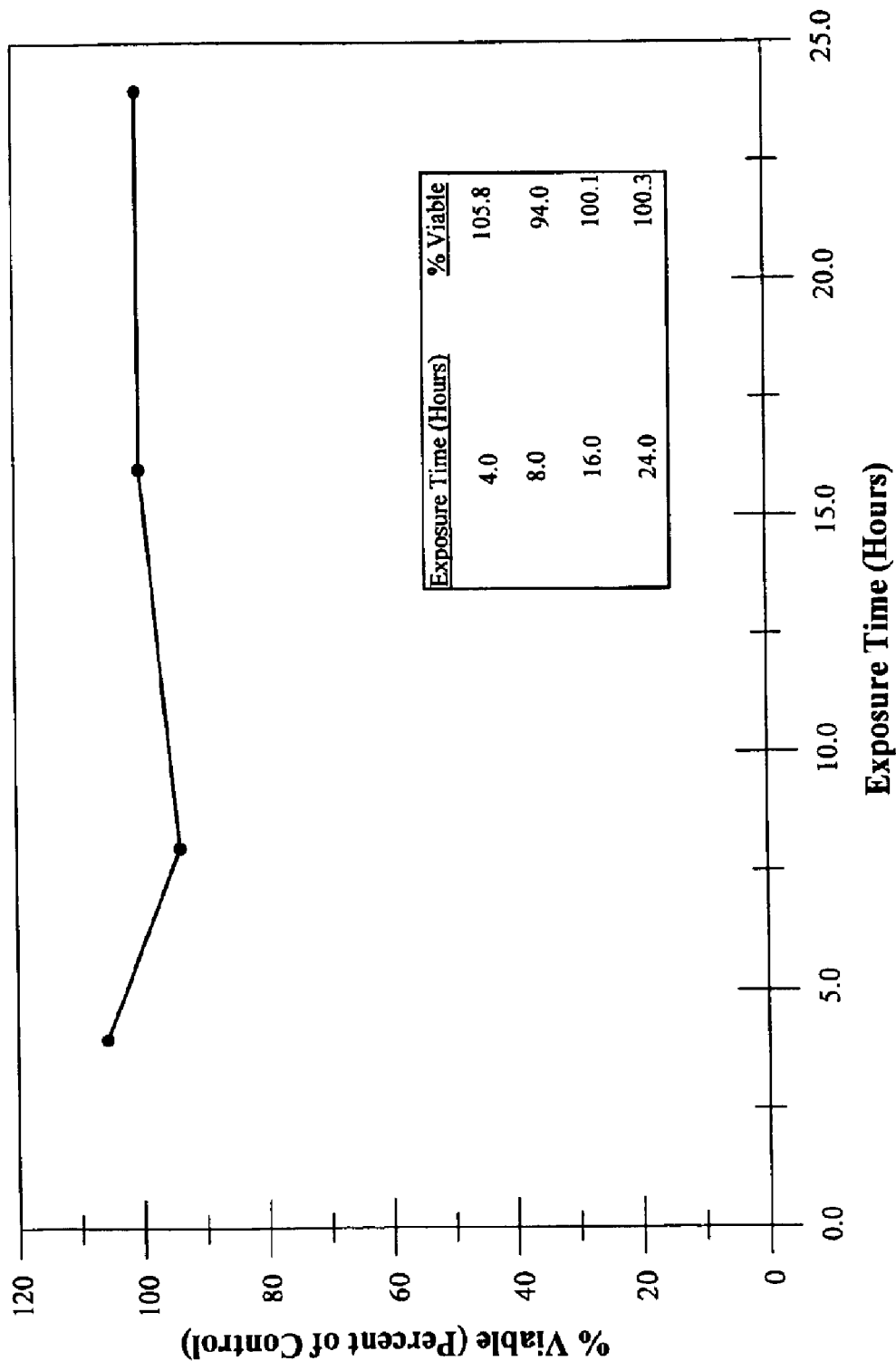

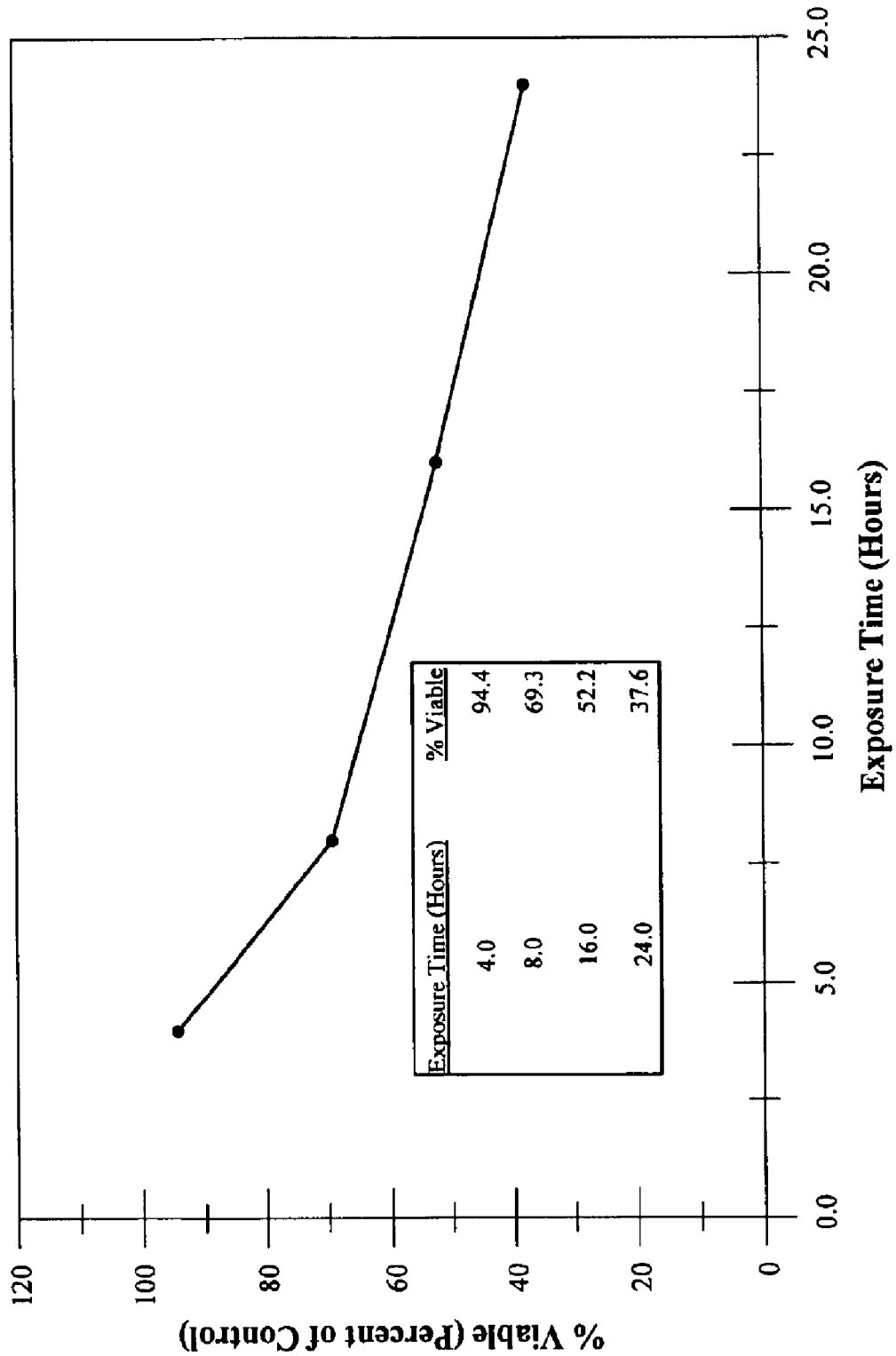
Figure 4: Epiderm Bioassay Results for State of the Art Warming Product (Prosensual)

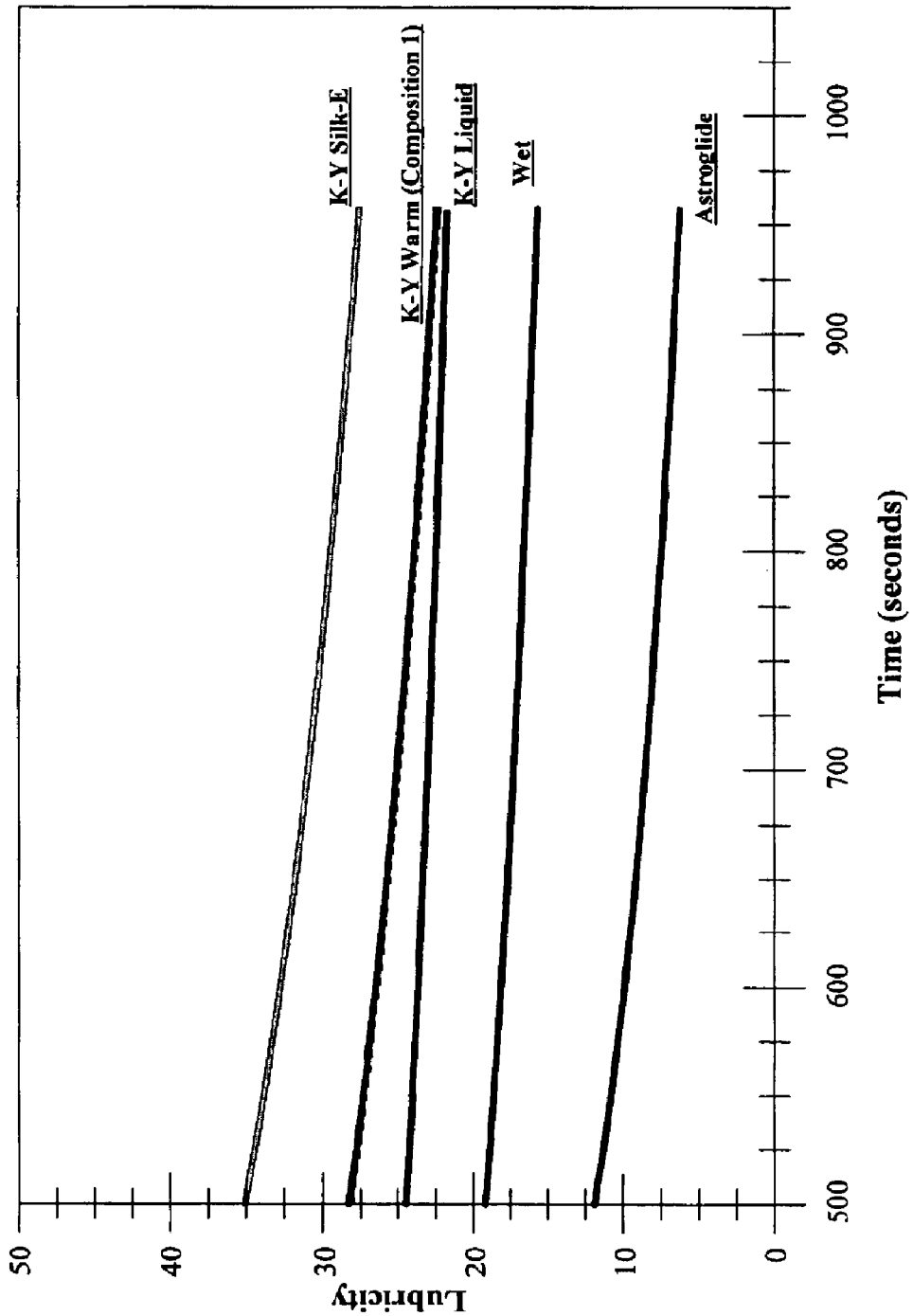
Figure 5: Lubricity Comparison of K-Y Silk-E, K-Y Warm (Composition 1), K-Y Liquid, Wet, and Astroglide

WARMING AND NONIRRITATING LUBRICANT COMPOSITIONS AND METHOD OF COMPARING IRRITATION

FIELD OF THE INVENTION

This invention relates to personal lubricant compositions that are warming and nonirritating when applied to the skin or mucous membranes, especially the vaginal or oral mucosa. The compositions of this invention are substantially anhydrous and contain one or more polyhydric alcohol. This invention also relates to the method that can be used to test and compare the irritation of the compositions of this invention and other personal lubricants known to the art.

BACKGROUND OF THE INVENTION

In the field of personal lubricants and medicaments applied to mucosal membranes, from time to time attempts have been made to overcome the problem of the perception of cold. When an individual applies personal lubricant or medicament such compositions to internal mucosal membranes, often an individual experiences an uncomfortable, cold feeling due to the difference in temperature between the body and the ambient temperature.

An appreciable number of personal lubricant compositions are known to the art. These compositions range from jellies to liquids to vaginal suppositories and vary from being aqueous to oils to silicone based. The majority of the compositions actually used today are aqueous jellies or aqueous liquids. Almost all personal lubricants known and available for use today are cold to touch, a feeling that can be uncomfortable.

A number of compositions are known to the trade or described in the literature that claim to impart a warming sensation upon application to the skin or mucosa. Some of these compositions use plant extracts which are irritating to the skin and mucous membranes and give a feeling or perception of warmth by virtue of their irritant action. Others claim to enhance blood flow in order to cause tissue warming. Still others are alleged to work on the principle of freezing point depression and are well suited for heating in a microwave or cooling in a refrigerator. There is one cosmetic composition rendered self-heating by inclusion of compound containing a boron-to-boron linkage, which reacts exothermally with water.

One example of a composition known to the trade, Prosensual™, distributed by Lexie Trading, Inc., Fairlaw, N.J., contains plant extracts such as Cinnamon cassia (Cinnamon), Zingiber officinalis (Ginger), Mint, Sandalwood, Orange and Clove, which are all known to be skin irritants. Such a composition has the disadvantage of causing irritation to the mucosa, which can be problematic in relation to the vaginal or oral mucosa as irritation may promote the growth of unwanted bacteria and cause infection.

Another current composition, WET™ Heating Massage Oil, distributed by International, Valencia, Calif., uses Retinyl Palmitate (Vitamin A Palmitate), *Prunus amygdalis* (Prunes), *Amara* (Almond), *Persica gratissima* (Avacado Oil), *Macadamia ternifulia* Seed Oil, Kakeri Nut Oil, *Helianthus annus* (hybrid Sunflower), *Cannabis sativa* (Hemp) Seed Oil and Aloe vera. Most of these ingredients are known irritants that are not suitable for use on mucous membranes.

U.S. Pat. No. 5,895,658, entitled "Delivery of L-Arginine to Cause Tissue Warming, Sustained Release of Nitric Oxide to treat effects of Diabetes, Stimulate Hair Growth and Heal Wounds," describes a preparation for producing enhanced blood flow in tissues thus causing beneficial effects, such as warming cold tissues of hands and feet.

U.S. Pat. No. 5,513,629 entitled "Microwavable Heat Releasing and Absorbing Compositions and Container, Pliable Gel Comprising Humectant, Freezing Point Depressant, Gel Sealer, Polyacrylamide Absorbent, Corn Starch Binder, Mineral Oil and Plasticizers, Durability, Efficacy" describes compositions that have a high vapor points and are, therefore, suited for heating in a microwave oven or cooling in a freezer and placement in a suitable container or vinyl package, such as a hot-and-cold pack, but not for human consumption or use.

However, none of the foregoing compositions are actually "warm", or at a relatively higher temperature than the ambient temperature of the product or the surrounding environment.

U.S. Pat. No. 4,110,426, entitled "Method of Treating Skin and Hair with a Self Heated Cosmetic, Organic Boron-Oxygen-Boron Compounds" describes non-aqueous compositions such as shaving creams, that are rendered self-heating by including therein a compound containing at least one boron-oxygen-boron linkage, such as triethoxyboroxine. The boron-containing compound reacts exothermally with water or other protic material to increase temperature. Such compositions are not suitable for vaginal or oral use due to the potential toxicity of boron-containing compounds to the human reproductive system (Fail P A, et al., *general, reproductive, developmental, and endocrine toxicity of boronated compounds.*, Reprod toxicol 12: 1, 1–18, January–February, 1998).

Physical energy forms have been utilized to enhance material transport across a membrane for therapeutic purposes. Such energy forms include electricity, ultrasound and thermal energy (e.g., heat-assisted drug delivery), (reviewed by Sun, in "Skin Absorption Enhancement by Physical Means: Heat, Ultrasound, and Electricity", *Transdermal and Topical Drug Delivery Systems*, Interpharm Press, Inc., 1997, pages 327–355). Local heating of a drug delivery system or formulation, as well as the skin or mucosal tissues, not only increases thermodynamic energy of drug molecules and membrane permeability to facilitate drug movement across a barrier membrane, it improves blood circulation in the tissue to expedite drug removal from the local tissue into the systemic circulation. Both processes leads to an enhanced absorption of the drug. Experimental evidence demonstrates that low-level heating (i.e., a tissue temperature of less than about 42° C.) significantly enhances percutaneous drug absorption.

U.S. Pat. No. 5,658,583 describes a heat-generating apparatus for improved dermal permeation of pharmaceuticals. The apparatus includes a thin drug formulation reservoir and a heat-generating chamber of oxidation reaction separated by a non-permeable wall. The drug formulation reservoir houses a predetermined amount of a formulation containing pharmaceutical agents. The heat-generating/temperature-regulating chamber includes a heat-generating medium consisting of carbon, iron, water and/or salt which is activated upon contact with oxygen in the air. However, a complicated heating device such as this is not suitable for use in the vaginal or oral cavity for obvious safety concerns.

Locally applied heat (such as an abdominal heating patch) has also been used to treat dysmenorrhea, or menstrual cramps, with demonstrated efficacy (Akin M D et al., *Continuous low-level topical heat in the treatment of dysmenorrhea.*, Obstet Gynecol 97: 3, 343–9, March, 2001).

U.S. Pat. No. 6,019,782 describes disposable thermal body pads with heat generation via an oxidation reaction intended for relieving menstrual pain when applied onto the abdominal skin. There is currently a commercial product in the U.S. market for dysmenorrhea treatment based on abdominal heating, ThermaCare® Air-Activated Heatwraps, Menstrual Cramp Relief patches manufactured by Procter &

Gamble (Cincinnati, Ohio). However, there are no products or description of internal localized heating to treat dysmenorrhea.

SUMMARY OF THE INVENTION

The compositions and methods of this invention relate to warming lubricant compositions that are non-toxic and non-irritating and that can be used as personal lubricants designed to come into contact with the skin or mucosa. When mixed with water, the compositions of this invention increase in temperature or generate warmth. This has a soothing effect on the tissues to which these compositions are applied.

The compositions of this invention may be applied to the skin or mucous membranes, preferably the vaginal or oral mucosa. The compositions of this invention are preferably substantially anhydrous and preferably contain at least one polyhydric alcohol.

We theorize that, when the polyhydric alcohols contained in the compositions of this invention come into contact with water or body moisture in humans, they react with the ambient water molecules to cause an increase in temperature or generate warmth, thus having a soothing effect on the tissues to which these compositions are applied.

Surprisingly, and contrary to the general belief that polyhydric alcohols in compositions are irritating to the mucosa, compositions of this invention containing such polyhydric alcohols have been found to be non-irritating. In fact, these compositions are very mild to the skin and mucous membranes. The compositions of this invention are soothing when applied to oral mucous membranes and may function to relieve minor irritation of the mouth and throat.

The combination of polyhydric alcohols in the compositions of this invention may also be used as a vehicle to solubilize otherwise insoluble drugs, including, but not limited to, antifungals, antibacterials, antivirals, analgesics, anti-inflammatory steroids, contraceptives, local anaesthetics, hormones and the like.

The compositions of this invention also preferably contain an insulating agent which functions to preserve the temperature increase by maintaining the heat within the composition after it has been applied to the skin or mucosa. More preferably, honey may be utilized as an insulating agent.

BRIEF DESCRIPTION OF THE DRAWINGS

FIG. 1 is a graph depicting the % viable Epiderm cells vs Exposure Time using the composition of Example 1.

FIG. 2 is a graph depicting the % viable Epiderm cells vs Exposure Time using the composition of Example 2.

FIG. 3 is a graph depicting the % viable Epiderm cells vs Exposure Time using a State-of-the-Art non-irritating Product (K-Y Liquid®).

FIG. 4 is a graph depicting the % viable Epiderm cells vs Exposure Time using a State-of-the-Art warming Product (Prosensual®)

FIG. 5 is a graph comparing the Lubricity vs Time (Seconds) of the composition of Example 1 and three leading Personal Lubricants on the market.

DETAILED DESCRIPTION OF THE PREFERRED EMBODIMENTS

The compositions of this invention are substantially anhydrous, preferably containing less than about 20% water, more preferably containing less than about 5% water and, most preferably, containing less than about 3% water. Preferably, the compositions of this invention contain at least one polyhydric alochol, and more preferably, two polyhydric alcohols. Preferably the polyhydric alcohol portion of the compositions of this invention one or more polyhydric alcohols such as alkylene glycols and others selected from the following group: glycerin, propylene glycol, butylene glycol, hexalene glycol or polyethylene glycol of various molecular weight and the like and/or combination thereof. More preferably, the compositions of this invention contain a polyethylene glycol; most preferably, the polyethylene glycol may be selected from the following group: polyethylene glycol 400 or polyethylene glycol 300. The compositions of this invention should contain polyhydric alcohols in an amount from about 80% to about 98% by weight of the composition.

The compositions of this invention preferably also contain an insulating agent. More preferably, the insulating agent should be honey or esters of isopropyl alcohol and saturated high molecular weight fatty acids such as myristic or palmitic acid, e.g., isopropyl myristate and isopropyl palmitate. The insulating agent should be present in the compositions of this invention in an amount of from about 1% to about 5% by weight of the composition.

The compositions of this invention are unexpectedly self-preserving and may not require a preservative. However, a preservative may be added to impart an additional guarantee against microbial growth. A preservative may be selected from preservatives known to those of skill in the art, including, but not limited to, one or more of the following: methylparaben, benzoic acid, sorbic acid, gallic acid, propylparaben or the like. The preservative may be present in the compositions of this invention in an amount from about 0.01% to about 0.75% by weight of the composition.

The compositions of this invention may also preferably contain an ester. More preferably, the ester is a fatty acid ester. Most preferably, the ester may include, but is not limited to: isopropyl stearate, isopropyl myristate, isopropyl palmitate, isopropyl laurate and the like. Most preferably, the ester is isopropyl myristate.

The compositions of this invention may contain one or more water-soluble cellulose-derived polymers, gums, chitosans or the like. Such polymers contribute to the viscosity and bioadhesiveness of the compositions of this invention. Preferably, such cellulose-derived polymers are hydroxyalkylcellulose polymers. More preferably, the hydroxyalkylcellulose polymer is hydroxypropylcellulose or Klucel®, available commercially from Hercules Incorporated, Wilmington, Del.

The polyhydric alcohols used in the compositions of this invention are theorized to be useful as warming and heat-generating agents. Honey functions as an insulating agent, protecting the compositions from becoming too cold. The ester, preferably a fatty acid ester, functions as an emollient and lubricant. The cellulose polymer is useful as a viscosity building agent. The compositions of this invention are unique in that they lubricate, warm and soothe the tissues of the user, especially the oral and vaginal mucous membranes, without conveying a feeling of cold. Moreover, they are smooth and lubricating.

The compositions of this invention may be a liquid, a semi-solid, or a solid depending upon the particular intended use thereof. The compositions of this invention may also be formulated into soft or hard gelatin capsules, suppositories and impregnated into fabrics or polymers.

The compositions of this invention may be used as personal lubricants which convey a feeling of warmth. The feeling of warmth generated by the compositions of this invention is soothing to the skin or mucous membranes where they are applied. The compositions of the invention also possess a sweet and pleasant taste, which is of particular benefit when these compositions are used orally.

The compositions of this invention may also be used as personal moisturizers, which convey a feeling of warmth when applied to vaginal or oral mucosa.

The compositions of this invention may also be used as a vehicle to deliver medication or other treatment agents to the biomembranes including, but not limited to, hormones, antimicrobial or antifungal agents and the like. The antifungal agents is preferably an azole or imidazole, including but not limited to, miconazole, econazole, terconazole, saperconazole, itraconazole, butaconazole, clotrimazole, tioconazole, fluconazole and ketoconazole, vericonazole, fenticonazole, sertaconazole, posaconazole, bifonazole, oxiconazole, sulconazole, elubiol, vorconazole, isoconazole, flutrimazole and their pharmaceutically acceptable salts and the like. Other antifungal agents may include an allylamine or one from other chemical families, including but not limited to, ternafine, naftifine, amorolfine, butenafine, ciclopirox, griseofulvin, undecyclenic acid, haloprogin, tolnaftate, nystatin, iodine, rilopirox, BAY 108888, purpuromycin and their pharmaceutically acceptable salts.

Another embodiment of the invention are compositions for vulvovaginal use containing one or more antibiotics. The antibiotic may be chosen from the group including, but not limited to, metronidazole, clindamycin, tinidazole, ornidazole, secnidazole, refaximin, trospectomycin, purpuromycin and their pharmaceutically acceptable salts and the like.

Another embodiment of the compositions of this invention include compositions for vulvovaginal use containing one or more antiviral agents. Antiviral agents may preferably include, but are not limited to, immunomodulators, more preferably imiquimod, its derivatives, podofilox, podophyllin, interferon alpha, reticolos, cidofovir, nonoxynol-9 and their pharmaceutically acceptable salts and the like.

Still other embodiments of the compositions of this invention are compositions that include one or more spermicides. The spermicides may preferably include, but are not limited to, nonoxynol-9, octoxynol-9, dodecaethyleneglycol monolaurate, Laureth 10S, and Methoxypolyoxyethyleneglycol 550 Laurate and the like.

Still other embodiments of the compositions of this invention are compositions containing antimicrobial agents. The antimicrobial agents may preferably include, but are not limited to, chlorohexidine gluconate, sodium polystyrene sulfonate, sodium cellulose sulfate, silver particles of micro- and sub-micrometer sizes, silver salts and other antibacterial agents known to the art.

Yet other embodiments of the compositions of this invention are compositions that may include local anesthetics. The local anesthetics may preferably include, but are not limited to, benzocaine, lidocaine, dibucaine, benzyl alcohol, camphor, resorcinol, menthol and diphenylhydramine hydrochloride and the like.

Compositions of the invention may also include plant extracts such as aloe, witch hazel, chamomile, hydrogenated soy oil and colloidal oatmeal, vitamins such as vitamin A, D or E and corticosteroids such as hydrocortisone acetate.

Another embodiment of the compositions and methods of this invention include compositions for vulvovaginal use containing one or more hormones for treating a decrease in estrogen secretion in the woman in need of estrogen replacement such as women with vaginal atrophy. The hormones may preferably include, but are not limited to, estrogen selected from the group consisting of estradiol, estradiol benzoate, estradiol cypionate, estradiol dipropionate, estradiol enanthate, conjugated estrogen, estriol, estrone, estrone sulfate, ethinyl estradiol, estrofurate, quinestrol and mestranol.

Another embodiment of the compositions and methods of this invention include compositions for vulvovaginal use containing one or more analgesics and/or nonsteroidal anti-inflammatory agents for treating dysmenorrhea or mentrual cramping. The analgesics and nonsteroidal anti-inflammatory agents may preferably include, but are not limited to, aspirin, ibuprofen, indomethacin, phenylbutazone, bromfenac, fenamate, sulindac, nabumetone, ketorolac, and naproxen and the like.

Yet another embodiment of the compositions and methods of this invention include compositions for oral and vulvovaginal use relates to a method of enhancing the absorption of active agents from the applied compositions into the mucosal membrane by increasing the composition and mucosal tissue temperature via interaction of the polyhydric alcohols in the compositions and moisture on the mucosa and subsequently released heat.

Yet another embodiment of the compositions of this invention include compositions for vulvovaginal use relates to compositions and methods for preventing and/or treating dysmenorrhea by intravaginal warming or heating. Preferably, the composition heats the intravaginal area to a temperature preferably between about 37° C. and about 42° C., more preferably between about 38° C. and about 41° C. The compositions of invention for use in such a method may optionally contain active agents such as analgesics and nonsteroidal anti-inflammatory agents for dysmenorrhea treatment. The composition of the invention may be administered directly into the vagina by an applicator, or be impregnated into vaginal devices such as tampon for intravaginal applications.

The compositions of this invention may be manufactured as a coating of a tampon, or dispersing throughout the absorbent tampon material, or enclosed inside as a core of a tampon. The compositions of this invention for the warming tampon for preventing and/or treating dysmenorrhea preferably include a mixture of polyethylene glycols of various molecular weights produced by The Dow Chemical Company (Midland, Mich.) under the trade names of CARBOWAX SENTRY PEG 300 NF, CARBOWAX SENTRY PEG 400 NF, CARBOWAX SENTRY PEG 600 NF, CARBOWAX SENTRY PEG 900 NF, CARBOWAX SENTRY PEG 1000 NF, CARBOWAX SENTRY PEG 1450 NF, CARBOWAX SENTRY PEG 3500 NF, CARBOWAX SENTRY PEG 4000 NF, CARBOWAX SENTRY PEG 4600 NF, and CARBOWAX SENTRY PEG 8000 NF. The compositions of this invention for dysmenorrhea prophylaxis and treatment may contain one or more water-soluble cellulose-derived polymers and gums that form gels around the polyhydric alcohols such as glycerin, propylene glycol and polyethylene glycols thus reducing the dissolution of the polyhydric alcohols, prolonging the salvation heat release, and regulating the elevated temperature in the preferred temperature range.

This invention also relates to a method of determining and comparing relative amounts of irritation caused by particular sources using the EpiDerm™ Skin Model Assay as described in Example 1, such as compositions applied to skin or mucosal cells. The following Example 1 exemplifies the use of the method of this invention.

EXAMPLE 1

EpiDerm™ Skin Model Assay to Test Irritation of Lubricants

The method designated as EpiDerm™ Skin Model assay uses the epithelial cells derived from human skin as target cells and is commercially available from the MatTek Corporation. This assay is described in Berridge, M. V., et al. (1996) *The Biochemical and Cellular Basis of Cell Proliferation Assays That Use Tetrazolium Salts*. Biochemica 4: 14–19. The test materials are applied directly to the epithelial cell culture surface. This test has not previously been used for determining toxicity of test materials. The toxicity of the test material is evaluated on the basis of relative tissue viability vs time. The actual Tissue Viability is determined by NAD(P)H-dependent microsomal enzyme reduction of MTT in control and test article treated cultures. The negative control used in this assay was deionized water and the positive control was Triton X-100. The exposed cell cultures were incubated for 4, 8, 16 and 24 hours and assayed for reduction of MTT. The data is presented below in FIGS. 1 through 4 in the form of Relative Survival (relative MTT reduction) versus Exposure Time. Products with higher relative survival rates are less toxic or less irritating while the ones with lower survival rates are more toxic or irritating.

FIGS. 1 through 4 summarize the results of Epiderm Skin Model Bioassay. The data is plotted as % Viable Cells vs the Exposure Time ranging from 4 to 24 hours. FIGS. 1 and 2 represent the results for two compositions of this invention, Composition 1 and Composition 2 respectively. FIG. 3 represents the results of K-Y® Liquid that is an established personal lubricant on the market. K-Y® Liquid is established as safe and nonirritating in animal and human testing and long-term human use history. Results for K-Y® Liquid showed 100.3% viable cells after 24 hour of exposure (FIG. 3).

Example 1 of the invention (FIG. 1) and Example 2 of the invention (FIG. 2) showed 91.1% and 96.9% viable cells respectively. FIG. 4 shows the results of a warming composition known to the trade. This product uses plant materials like cinnamon, clove, ginger cloves and orange and others for a warming sensation. The results show only 37.6% viable cells after 24 hours of exposure to this product. This indicates that such compositions will be irritating to the skin and mucous membranes. Compositions 1 and 2 of this invention, with 91.1% and 96.9% viable cells respectively, will be practically nonirritating. Positive control (Triton X-100) has only 22.4% viable cells at the 8-hour interval.

EXAMPLE 2

Generation of Warmth

The compositions of this invention are anhydrous and contain one or more polyhydric alcohol. When combined with water, the polyhydric alcohols used in the compositions of this invention generate an increase in temperature that has a soothing effect on the tissues these compositions are applied. In actual use the compositions of the invention interact with the moisture of the vaginal or oral mucosa, thereby increasing the temperature or generating feeling of warmth.

The "Generation of warmth" data summarized in Table 1 below, was generated by mixing 20 ml of each of the ingredients in Composition 1 and Composition 1 of this invention with 20 ml of water. The temperature of the product and that of water were recorded before water was added to the product. After the addition of water the mixture was mixed for two minutes and the actual temperature was recorded. Glycerin, Propylene Glycol and Honey are the ingredients in Composition 1. It is clear from Table 1. that when mixed with water the temperature of the mixture rises by 9.0° F. for Glycerin, 13.5° F. for Propylene Glycol, 17.0° F. for Polyethylene Glycol 400 and 12.5° F. for composition Example 1 of this invention. The calculated rise in temperature for Composition 1, based on the rise in temperature and the % w/w quantity of each individual ingredient in the composition was 10.875° F. The actual recorded temperature rise for Composition 1. was 12.5° F. which is 1.625° F. higher than expected which indicates that there is an unexpected increase in temperature resulting from the combination of ingredients.

GENERATION OF WARMTH (RISE IN TEMPERATURE ° F.) DATA BY MIXING EQUAL QUANTITY OF EACH PRODUCT WITH WATER

| Product Name | Temperature of the Product (° F.) | Temperature of Water (° F.) | Average Expected Temperature (° F.) | Actual Temperature (° F.) | Rise in Temperature (° F.) (Expected Minus Actual) |
| --- | --- | --- | --- | --- | --- |
| Glycerin Assay | 69.0 | 71.0 | 70.0 | 79.0 | 9.0 |
| Propylene Glycol Assay | 72.4 | 71.0 | 71.7 | 85.2 | 13.5 |
| Honey | 74.0 | 71.0 | 72.5 | 74.0 | 1.5 |
| K-Y Warm ® | 74.0 | 71.0 | 72.5 | 85.0 | 12.5 |
| Isopropyl Myristate | 75.0 | 74.1 | 74.5 | 75.2 | 0.7 |
| Polysorbate 60 | 70.9 | 74.1 | 72.5 | 83.1 | 10.6 |
| Polyethylene Glycol 400 | 72.0 | 71.0 | 71.5 | 88.5 | 17.0 |

Calculated Rise in Temperature: In order to determine the expected rise in temperature from each composition, the percentage of each component in such composition was multiplied by the temperature increase generated by such component alone to obtain its expected contribution to the temperature increase. These values were added together to calculate the total expected temperature rise. These values were then compared with the actual temperature rise generated by each composition. For example, the calculated rise in temperature generated by the "K-Y Warm®" composition in the table above was found as follows and compared with the actual temperature rise to determine the unexpectedly higher generation of warmth of the composition:

| | |
|---|---|
| Propylene Glycol (50% of 13.5) = | 6.75 |
| Glycerin (45% of 9.0) = | 4.05 |
| Honey (5% of 1.5) = | 0.075 |
| Total | 10.875 |
| Difference: 12.5 − 10.875 = 1.625 | |

EXAMPLE 3

Effect of Water Content on Generation of Warmth

On contact with moisture or water the heat of solution is responsible for the warming action of the compositions of this invention. There is a concern that accidental contamination with water or prolonged exposure to excessive moisture, the warming capacity of the product may be adversely effected. According to this example, water was added to compositions of this invention varying from about 1% to about 10% as outlined in Table 2 below. The contents were thoroughly mixed and the samples were allowed to stay at room temperature for 24 hour following which the generation of warmth was determined as outlined in the following paragraph. The results show that rise in temperature is proportionately decreased depending on the quantity of water added but there is still an 8.5° F. increase in temperature at about 10% water addition.

The results of this example are set forth in Table 2 below.

TABLE 2

Effect Of Water Content On Generation Of Warmth For K-Y Warm ®.

| Product Name | Temperature of the Sample (° F.) | Temperature of Water (° F.) | Average Expected Temperature (° F.) | Actual Temperature (° F.) | Rise in Temperature (° F.) (Expected Minus Actual) |
|---|---|---|---|---|---|
| No Water | 73.80 | 70.00 | 71.90 | 83.50 | 11.60 |
| 1% Water | 73.90 | 70.00 | 71.95 | 82.20 | 10.25 |
| 2% Water | 72.30 | 70.00 | 71.95 | 81.70 | 9.85 |
| 3% Water | 72.30 | 70.00 | 71.15 | 80.40 | 9.25 |
| 4% water | 72.20 | 70.00 | 71.10 | 80.70 | 9.60 |
| 5% Water | 71.60 | 70.00 | 70.80 | 80.40 | 9.60 |
| 6% Water | 71.60 | 70.00 | 70.80 | 80.40 | 9.60 |
| 7% Water | 71.50 | 70.00 | 70.75 | 80.20 | 9.45 |
| 8% Water | 71.60 | 70.00 | 70.80 | 80.20 | 9.40 |
| 9% Water | 70.90 | 70.00 | 70.45 | 79.50 | 9.05 |
| 10% Water | 70.50 | 70.00 | 70.25 | 79.00 | 8.50 |

EXAMPLE 4

Perception of Warmth in Human Use

A Human Use Study was conducted with 246 subjects. The data generated by this study are summarized below in Table 2. The subjects were asked to use compositions of this invention. They were asked three questions regarding the perception of warmth while using the product, as follows:

1. Does it warm on contact?
2. Does it feel warm?
3. Does it not feel cold?

The subjects were asked to register their response as Excellent, Very Good, Good, Fair and Poor. The positive responses are summarized in Table 2.

TABLE 3

PERCEPTION OF WARMTH IN HUMAN USE STUDY WITH 246 HUMAN SUBJECTS USING COMPOSITION EXAMPLE 1 OF THE INVENTION

| QUESTION ASKED | POSITIVE RESPONSE (%) |
|---|---|
| Warms on Contact | |
| Excellent | 25.12 |
| Very Good | 31.88 |
| Good | 24.64 |
| Total | 81.64 |
| Feels Warm | |
| Excellent | 30.88 |
| Very Good | 28.92 |
| Good | 25.98 |
| Total | 85.78 |
| Does Not Feel Cold | |
| Excellent | 54.37 |
| Very Good | 29.61 |
| Good | 10.19 |
| Total | 94.53 |

As set forth in Table 3 above, 81.64% of the subjects registered a positive response that the product "warms on contact", 85.78% subjects felt that the product "feels warm" while 94.53% subjects registered that the product "does not feel cold".

EXAMPLE 4

Comparison of Lubricity

Ahmad et al. in U.S. Pat. No. 6,139,848, which is hereby incorporated herein by reference, describe a method to test lubricity of various personal lubricants known to the trade. In the described test method, the lubricity of various marketed personal lubricants was determined over a period of 300 seconds (5 minutes). The lubricity data disclosed in this patent indicates that K-Y Liquid® lubricant had a higher lubricity and was longer lasting during the 300 seconds test period than the competitive products. The lubricity data set forth in U.S. Pat. No. 6,139,848 has a negative (−) sign during the "push" and positive (+) sign during the "pull" phase of the experiment. Compositions of this invention were tested using the lubricity test set forth in U.S. Pat. No. 6,129,848. However, the test duration was successfully extended to 16 minutes (960 seconds) and the data was treated to "curve-fit" to eliminate the negative (−) sign. The lubricity data for the composition 1 of this invention is compared with the data for K-Y Liquid® in FIG. 5. The data indicate that Composition 1 of this invention has a higher lubricity as compare to K-Y Liquid® and that Composition 1 maintains the high lubricity for an extended period of 16 minutes (960 minutes) and is therefore longer lasting.

EXAMPLES 5–9

Compositions of the Invention

The following compositions of this invention were made as follows: first, propylene glycol and glycerin were mixed. A preservative and the insulating agent were then added to the mixture in the same container. The mixture was then heated to from about 35° C. to about 45° C. to completely dissolve the preservative. The mixture was then cooled.

| Composition 1: | |
|---|---|
| Propylene Glycol | 50.00% |
| Glycerin | 45.00% |
| Honey | 5.00% |
| Composition 2: | |
| Propylene Glycol | 50.00% |
| Glycerin | 20.00% |
| Isopropyl Myristate | 27.00% |
| Polysorbate 60 | 3.00% |
| Composition 3: | |
| Propylene Glycol | 95.00% |
| Honey | 5.00% |
| Composition 4: | |
| Propylene Glycol | 50.00% |
| Glycerin | 20.00% |
| Isopropyl Myristate | 29.50% |
| Klucel HF | 0.50% |
| Composition 5: | |
| Propylene Glycol | 99.50% |
| Klucel HF | 0.50% |
| Composition 6: | |
| Propylene Glycol | 49.80% |
| Glycerin | 45.00% |
| Honey | 5.00% |
| Preservative | 0.20% |
| Composition 7: | |
| Miconazole Nitrate | 2.00% |
| Propylene Glycol | 49.80% |
| Glycerin | 43.00% |
| Honey | 5.00% |
| Preservative | 0.20% |
| Composition 8: | |
| Fluconazole | 2.00% |
| Propylene Glycol | 49.80% |
| Glycerin | 43.00% |
| Honey | 5.00% |
| Preservative | 0.20% |
| Composition 9: | |
| Metronidazole | 3.00% |
| Propylene Glycol | 49.80% |
| Glycerin | 42.00% |

-continued

| | |
|---|---|
| Honey | 5.00% |
| Preservative | 0.20% |

What is claimed is:

1. A substantially anhydrous lubricant composition comprising at least one polyhydric alcohol and an insulating agent wherein said insulating agent is honey.

2. A method of providing personal lubrication to a human's vaginal mucosa comprising applying to the vaginal mucosa a composition comprising from about 80 % to about 98 % by weight polyhydric alcohol, from about 1 to about 5 % weight insulating agent, an insulating agent selected from the group consisting of honey, isopropyl myristate and isopropyl palmitate and less than about 20 % by weight water, composition conveying a feeling of warmth upon application.

3. A substantially anhydrous composition comprising at least one polyhydric alcohol and an insulating agent selected from the group consisting of honey and isopropyl palmitate.

4. A composition according to claim 3 wherein said composition further comprises a preservative.

5. A composition according to claim 3 wherein said composition further comprises a bioadhesive agent.

6. A composition according to claim 3 wherein said polyhydric alcohol is selected from the group consisting of: glycerin, alkylene glycol, polyethylene glycol and a mixture thereof.

7. A composition according to claim 6 wherein said alkylene glycol is selected from the group consisting of: propylene glycol, butylene glycol and hexalene glycol.

8. A composition according to claim 6 wherein said polyethylene glycol is selected from the group consisting of polyethylene glycol 300, polyethylene glycol 400 and a mixture thereof.

9. A composition according to claim 3 wherein said composition further comprises an antimicrobial agent.

10. A composition according to claim 9 wherein said antimicrobial agent is an antifungal agent.

11. A composition according to claim 9 wherein said antimicrobial agent is an antibacterial agent.

12. A composition according to claim 9 wherein said antimicrobial agent is an antiviral agent.

13. A composition according to claim 3 wherein said composition further comprises a spermicide.

14. A composition according to claim 3 wherein said composition further composes a local anesthetic.

15. A method of treating or preventing dysmenorrhea comprising applying intravaginally a composition comprising a substantially anhydrous lubricant composition comprising at least one polyhydric alcohol and an insulating agent selected from the group consisting of honey and isopropyl palmitate.

16. A composition comprising from about 80% to about 98% by weight polyhydric alcohol from about 1 to about 5% by weight insulating agent, an insulating agent selected from the group consisting of honey, isopropyl myristate and isopropyl palmitate and less than about 20% by weight water.

17. A composition according to claim 16 wherein said composition comprises from about 80% in about 98% by weight polyhydric alcohol and from about 1 to about 5% by weight insulating agent selected from the group consisting of honey and isopropyl palmitate and less than about 5 % by weight water.

18. A composition according to claim 17 wherein said composition comprises from about 80% to about 98% by weight polyhydric alcohol and from about 1 to about 5 % by weight insulating agent selected from the group consisting of honey and isopropyl palmitate and less than about 1 % by weight water.

19. A method of providing personal lubrication to a human's oral or vaginal mucosa comprising applying to the oral or vaginal mucosa a composition comprising a substantially anhydrous lubricant composition which conveys a feeling of warmth upon application comprising at least one polyhydric alcohol and an insulating agent selected from the group consisting of honey and isopropyl palmitate.

20. A method of providing personal lubrication to a human's vaginal mucosa comprising applying to the vaginal mucosa a composition comprising a substantially anhydrous lubricant composition which conveys a feeling of warmth upon application comprising at least one polyhydric alcohol and an insulating agent selected from the group consisting of honey and isopropyl palmitate.

21. A method according to claim 20 wherein said polyhydric alcohol is selected from the group consisting of: glycerin, alkylene glycol, polyethylene glycol and a mixture thereof.

22. A method according to claim 21 wherein said alkylene glycol is selected from the group consisting of: propylene glycol, butylene glycol and hexalene glycol.

23. A method according to claim 20 wherein said composition comprises from about 80 % to about 98 % by weight polyhydric alcohol, from about 1 to about 5 % by weight insulating agent, an insulating agent selected from the group consisting of honey and isopropyl palmitate and less than about 20 % by weight water.

24. A method of providing personal lubrication to a human's vaginal mucosa comprising applying to the vaginal mucosa a composition comprising a substantially anhydrous lubricant composition which conveys a feeling of warmth upon application comprising about 50 % by weight propylene glycol, about 45 % by weight glycerin and about 5 % by weight honey.

25. A composition comprising about 50 % by weight propylene glycol, about 45 % by weight glycerin and about 5 % by weight honey.

26. A composition according to claim 1 wherein said composition further comprises a preservative.

27. A composition according to claim 1 wherein said composition further comprises a bioadhesive agent.

28. A composition according to claim 1 wherein said polyhydric alcohol is selected from the group consisting of: glycerin, alkylene glycol, polyethylene glycol and a mixture thereof.

29. A composition according to claim 1 wherein said alkylene glycol is selected from the group consisting of: propylene glycol, butylene glycol and hexalene glycol.

30. A composition according to claim 29 wherein said polyethylene glycol is selected from the group consisting of polyethylene glycol 300, polyethylene glycol 400 and a mixture thereof.

31. A composition according to claim 1 wherein said composition further comprises a spermicide.

* * * * *